US011278766B2

(12) United States Patent
Lee (10) Patent No.: US 11,278,766 B2
(45) Date of Patent: Mar. 22, 2022

(54) REHABILITATION SYSTEM PERFORMING REHABILITATION PROGRAM USING WEARABLE DEVICE AND USER ELECTRONIC DEVICE

(71) Applicant: EXOSYSTEMS INC., Seoul (KR)

(72) Inventor: Hooman Lee, Seoul (KR)

(73) Assignee: EXOSYSTEMS INC., Seoul (KR)

( * ) Notice: Subject to any disclaimer, the term of this patent is extended or adjusted under 35 U.S.C. 154(b) by 0 days.

(21) Appl. No.: 17/054,628

(22) PCT Filed: Aug. 10, 2018

(86) PCT No.: PCT/KR2018/009216
§ 371 (c)(1),
(2) Date: Nov. 11, 2020

(87) PCT Pub. No.: WO2020/027360
PCT Pub. Date: Feb. 6, 2020

(65) Prior Publication Data
US 2021/0162262 A1 Jun. 3, 2021

(30) Foreign Application Priority Data
Aug. 2, 2018 (KR) ........................ 10-2018-0090391

(51) Int. Cl.
*A63B 24/00* (2006.01)
*A61N 1/36* (2006.01)
(Continued)

(52) U.S. Cl.
CPC ........ *A63B 24/0075* (2013.01); *A61N 1/0456* (2013.01); *A61N 1/0492* (2013.01); *A61N 1/36003* (2013.01); *A61N 1/36031* (2017.08); *A61N 1/36034* (2017.08); *A63B 23/0494* (2013.01); *A63B 71/0622* (2013.01); *G16H 20/30* (2018.01); *G16H 40/67* (2018.01); *A61B 5/389* (2021.01); *A63B 2071/0636* (2013.01); *A63B 2220/24* (2013.01); *A63B 2230/60* (2013.01)

(58) Field of Classification Search
CPC ............ A63B 24/0075; A61N 1/36031; A61N 1/36304
USPC .......................................................... 607/3
See application file for complete search history.

(56) References Cited

U.S. PATENT DOCUMENTS

2017/0340504 A1* 11/2017 Sanz Merodio ..... A61H 1/0262

FOREIGN PATENT DOCUMENTS

KR 10-2012-0057081 A 6/2012
KR 10-2015-0049145 A 5/2015

* cited by examiner

*Primary Examiner* — Nadia A Mahmood
(74) *Attorney, Agent, or Firm* — Goldilocks Zone IP Law (57) ABSTRACT

A rehabilitation system according to an embodiment of the present invention includes a wearable device for measuring rehabilitation exercise information of a user and a user electronic device receiving the rehabilitation exercise information from the wearable device and driving an avatar training program. The user electronic device may receive the avatar training program recommended based on user personal information and the rehabilitation exercise information from a rehabilitation program recommendation server. According to the present invention, a rehabilitation effect can be enhanced by performing a rehabilitation exercise according to a rehabilitation program suitable for a user using a wearable device and a user electronic device.

10 Claims, 10 Drawing Sheets (51) Int. Cl.
*G16H 20/30* (2018.01)
*G16H 40/67* (2018.01)
*A61N 1/04* (2006.01)
*A63B 23/04* (2006.01)
*A63B 71/06* (2006.01)
*A61B 5/389* (2021.01)

REHABILITATION SYSTEM PERFORMING REHABILITATION PROGRAM USING WEARABLE DEVICE AND USER ELECTRONIC DEVICE

This invention was made with Government support under Project Identification No.: 1711138172, Detailed Project No.: KMDF_PR_20200901_0101-01, Name of Department: Korea Medical Device Development Fund(KMDF), Project Director: Lee Hooman, Name of project performing organization: ExoSystems Inc., Project period: Mar. 1, 2021-Feb. 28, 2022, Project name: Development of artificial intelligence-based personalized exercise management platform and service to improve muscle function and prevent muscle loss in middle-aged people, Contribution rate: 100%.

CROSS-REFERENCE TO RELATED APPLICATIONS

The present application claims priority under 37 U.S.C. § 371 to International Patent Application No. PCT/KR2018/009216, filed Aug. 10, 2018, which claims priority to and the benefit of Korean Patent Application No. 10-2018-0090391, filed on Aug. 2, 2018. The contents of these applications are hereby incorporated by reference in their entireties.

TECHNICAL FIELD

The present invention relates to a rehabilitation system, in more detail relates to a rehabilitation system for performing a rehabilitation program using a wearable device and a user electronic device.

BACKGROUND ART

Due to untimely accidents or aging, such as damage to the muscles around the joint or joint can occur. In order to restore the range of motion (ROM) of the leg, rehabilitation exercises may be performed after surgery, or rehabilitation exercises may be performed without surgery. However, conventional rehabilitation exercises are repetitive and can be boring and painful. Therefore, the existing repetitive rehabilitation exercise has a problem that the rehabilitation period increases or the rehabilitation effect decreases.

In order to solve the above-mentioned problems, a rehabilitation exercise method linked to a game using a rehabilitation robot and a rehabilitation exercise method linked to a game using a 3D motion camera have been proposed. However, the rehabilitation exercise method using a rehabilitation robot is expensive, and the rehabilitation exercise method using a 3D motion camera has a disadvantage in that it cannot accurately measure the patient's movement. In addition, since the above-described rehabilitation exercise methods have space limitations, there is a problem that the patient cannot perform the rehabilitation exercise at home and must visit a specific place such as a hospital.

DISCLOSURE

Technical Problem

The present invention is to solve the above-described technical problem. The present invention is to provide a rehabilitation system capable of easily performing rehabilitation exercises without space constraints using a wearable device and a user electronic device.

Technical Solution

A rehabilitation system according to an embodiment of the present invention comprises a wearable device measuring user's rehabilitation exercise information; and a user electronic device receiving the rehabilitation exercise information from the wearable device and driving an avatar training program. wherein the user electronic device is provided the avatar training program recommended based on user personal information from a rehabilitation program recommendation server.

In an embodiment, the wearable device includes a first body part worn on a thigh part and a second body part connected to the first body part through a cable and worn on the shank part. Each of the first and second body parts has an electrical stimulation part for applying an electrical stimulation. The first body part measures the rehabilitation exercise information by generating an electrical stimulation signal of the nerve dominant muscle for functional electrical stimulation (FES), measuring an electromyography (EMG), and measuring a range of motion (ROM) of the joint angle.

As an embodiment, the user electronic device may execute the avatar training program and evaluate the user's program performance capability based on user state information. The user electronic device may control the wearable device to reach the program level by generating an FES signal when the user's program performance capability is less than the program level.

Another aspect of the rehabilitation system according to an embodiment of the present invention includes a wearable device measuring user's rehabilitation exercise information; a user electronic device receiving the rehabilitation exercise information from the wearable device and driving a gamified rehabilitation program; and a rehabilitation program recommendation server receiving user personal information and the rehabilitation exercise information from the wearable device or the user electronic device, recommending one or more gamified rehabilitation programs from among a plurality of rehabilitation programs based on the user personal information and the rehabilitation exercise information, and providing the recommended gamified rehabilitation program to the user electronic device.

As an embodiment, the wearable device generates an electrical stimulation signal of a nerve dominant muscle for functional electrical stimulation (FES), measures an electromyogram (EMG), and measures a range of motion (ROM) of the joint angle, so that the rehabilitation exercise Information can be measured.

Advantageous Effects

The rehabilitation system according to an embodiment of the present invention may increase a rehabilitation effect by performing a rehabilitation exercise according to a rehabilitation program suitable for a user using a wearable device and a user electronic device.

BEST MODE

Figure 5:
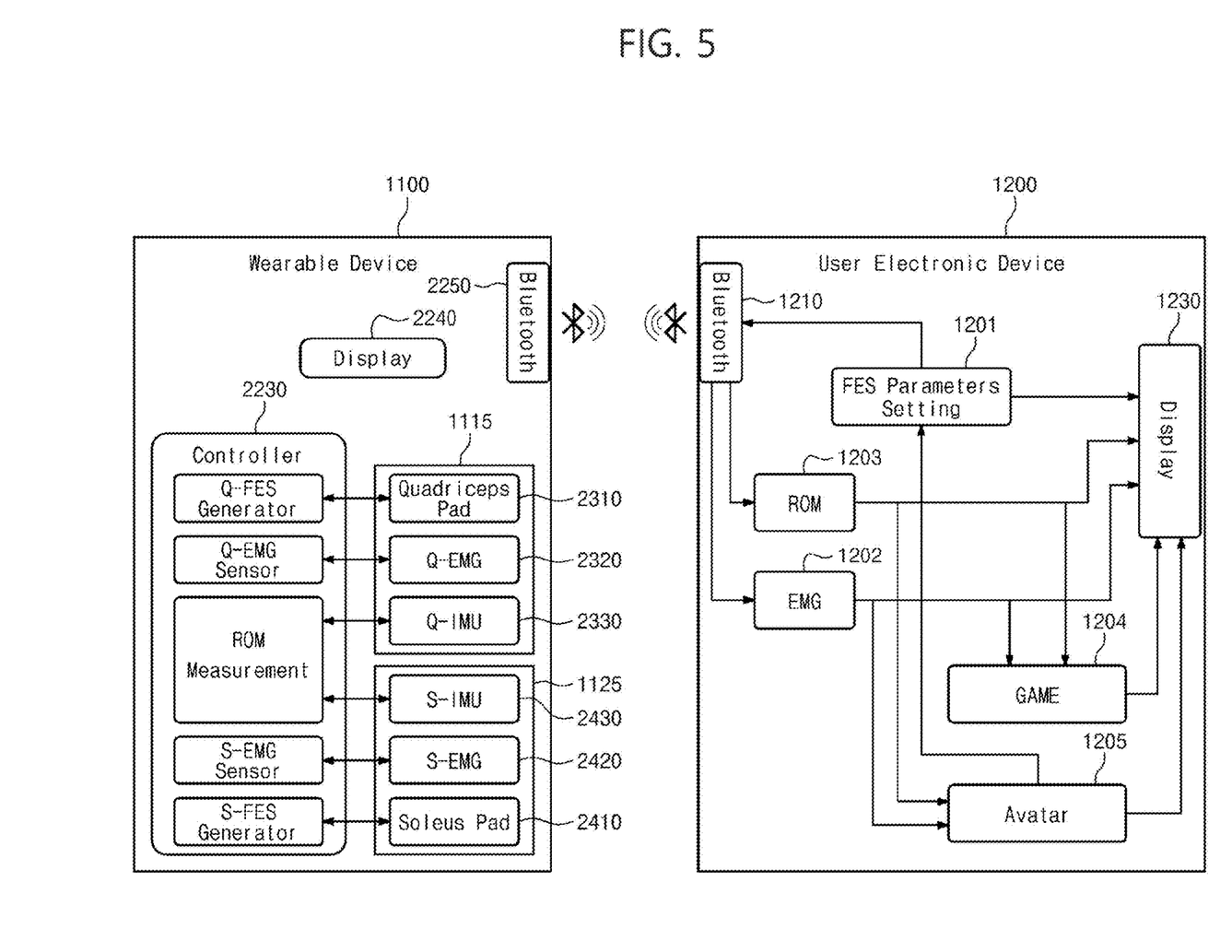
FIG. 5 is a block diagram illustrating an exemplary software structure of the user electronic device shown in FIG. 1.

FIG. 5 shows the best mode for implementing the present invention.

MODE FOR INVENTION

In the following, embodiments of the present invention will be described clearly and in detail to the extent that a person having ordinary knowledge in the technical field of the present invention can easily implement the present invention.

Figure 1:
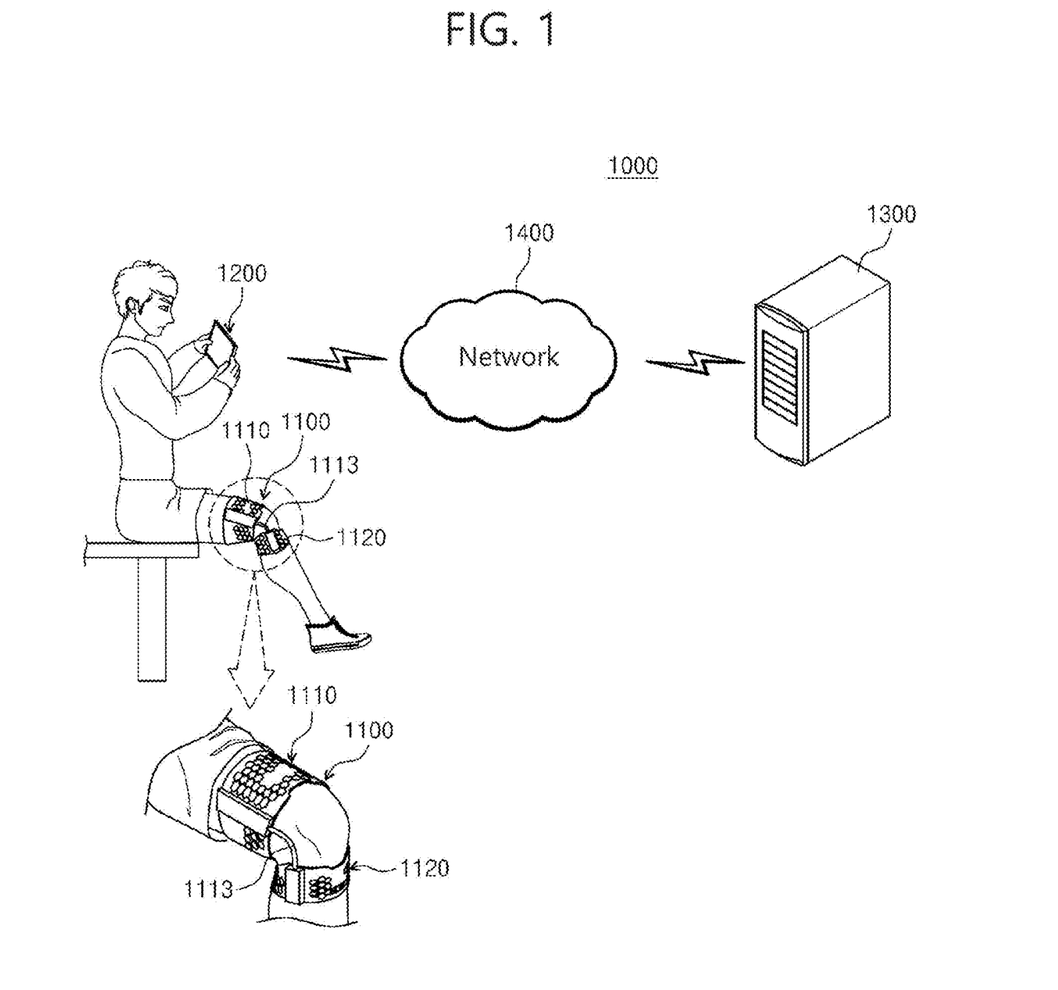
FIG. 1 is a block diagram illustrating an exemplary rehabilitation system according to an embodiment of the present invention.

FIG. 1 is a block diagram illustrating an exemplary rehabilitation system according to an embodiment of the present invention. Referring to FIG. 1, the rehabilitation system 1000 may include a wearable device 1100, a user electronic device 1200, and a rehabilitation program recommendation server 1300.

The wearable device 1100 may be worn on the user's body. The wearable device 1100 may help rehabilitation exercise by applying stimulation to the user's body. The wearable device 1100 may be used for muscle strengthening or other exercises in addition to rehabilitation exercises.

Referring to FIG. 1, the wearable device 1100 may include the first and second body part 1110, 1120. The first and second body part 1110, 1120 may be connected to a wired or wireless. In the example of FIG. 1, the first body part 10 is used for the thigh, and the second body part 1120 is used for the shank. The wearable device 1100 may also be used near joints other than the leg. For example, it can be used for wrists, elbows, shoulders, necks, waists, ankles, etc.

The wearable device 1100 may measure rehabilitation exercise information of a user and transmit the measured value to the user electronic device 1200. Here, the rehabilitation exercise information may include a user's range of motion, a joint rotation direction, a joint rotation speed and acceleration, a torque applied to a joint, a surface electromyogram, a rehabilitation exercise time, or the number of repetitions of a user's rehabilitation. The wearable device 1100 may be connected to the user electronic device 1200 by wire or wirelessly.

The user electronic device 1200 may receive rehabilitation exercise information from the wearable device 1100 and receive a rehabilitation program from the rehabilitation program recommendation server 1300. Here, the rehabilitation program may be a game-based rehabilitation program to help the user's rehabilitation exercise. The user electronic device 1200 may indicate in real time how much the user has performed the rehabilitation exercise by referring to the rehabilitation exercise information. In addition, the user electronic device 1200 may transmit rehabilitation exercise information to the rehabilitation program recommendation server 1300 through the network 1400.

The user electronic device 1200 may be a mobile phone, a smart phone, a tablet, a TV, or a personal computer (PC). The user electronic device 1200 is not limited to the above, and may be any type of electronic device capable of driving a rehabilitation program and providing an interface of a rehabilitation program to a user on a display.

The rehabilitation program recommendation server 1300 may be connected to the user electronic device 1200 through the network 1400. The rehabilitation program recommendation server 1300 may receive rehabilitation exercise information from the wearable device 1100 or the user electronic device 1200. The rehabilitation program recommendation server 1300 may recommend a rehabilitation program suitable for a user among a plurality of pre-stored rehabilitation programs by referring to the received rehabilitation exercise information. The rehabilitation program recommendation server 1300 may transmit a rehabilitation program suitable for a user to the user electronic device 1200 through the network 1400.

Figure 2:
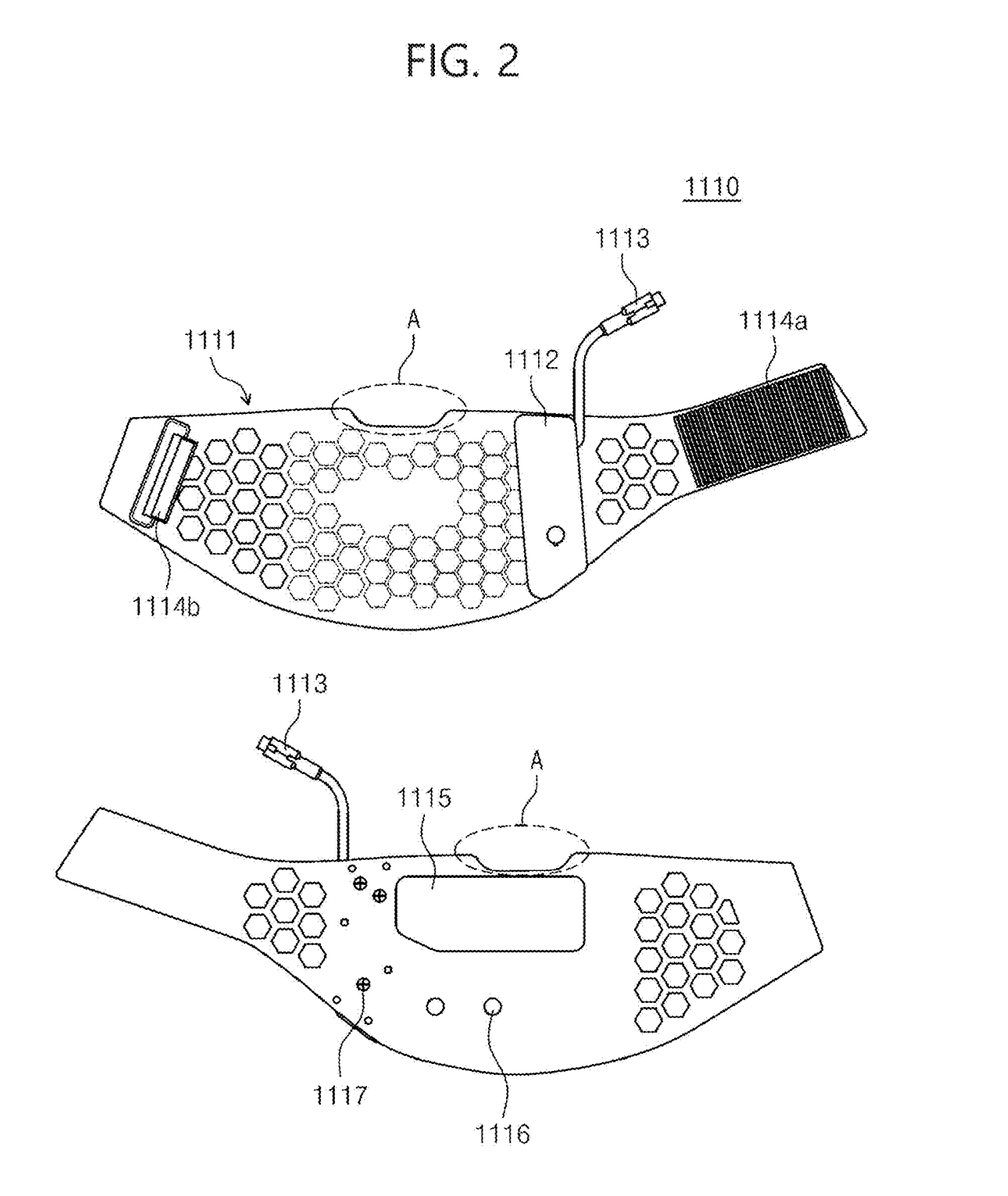
FIGS. 2 and 3 are views respectively exemplarily showing first and second body parts of the wearable device shown in FIG. 1.
Figure 3:
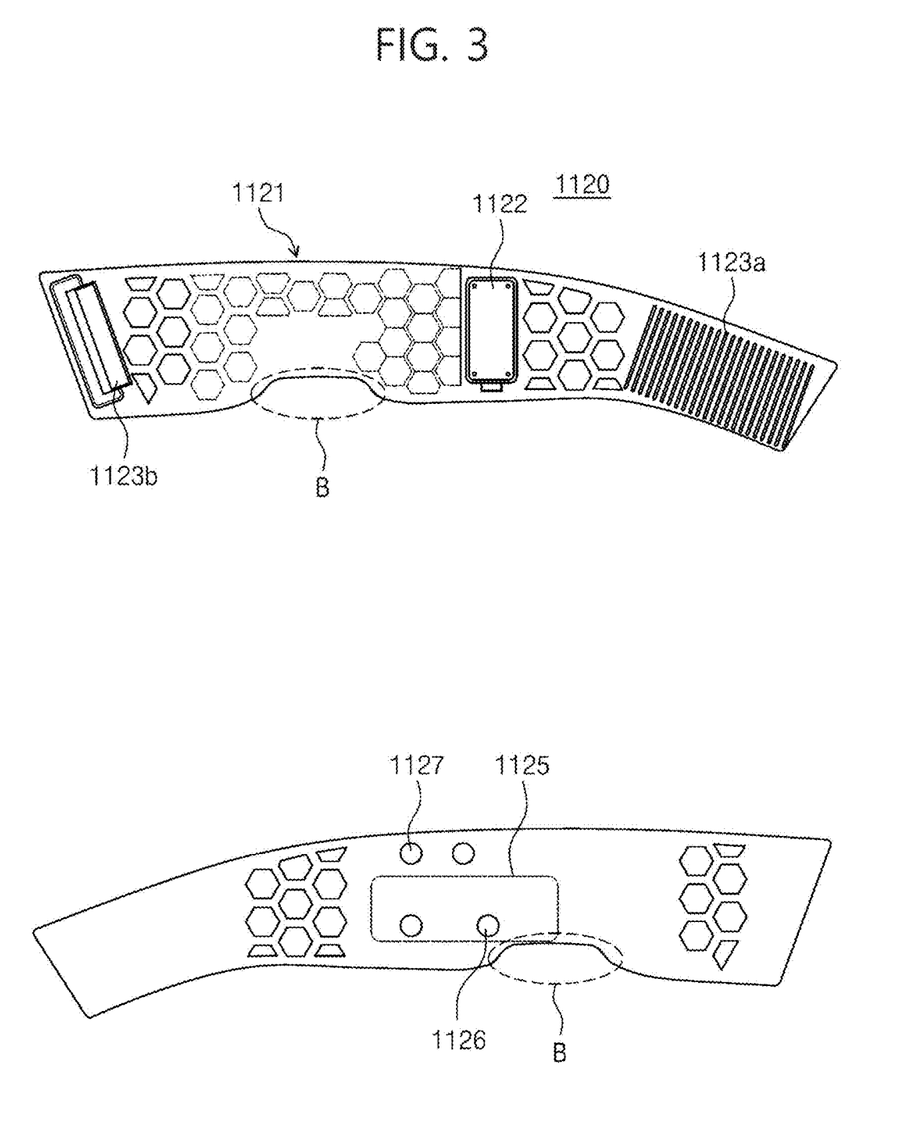

FIGS. 2 and 3 are views respectively exemplarily showing first and second body parts of the wearable device shown in FIG. 1. The first body part 1110 may be a thigh body, and the second body part 1120 may be a shank body. In FIGS. 2 and 3, the FIG. below is the inner part in close contact with the thigh or shank, and the FIG. above is the outer part seen when worn.

The first and second body parts 1110 and 1120 may support a user's knee joint. The first body part 1110 may support the thigh, and the second body part 1120 may support the shank. The first and second body parts 1110 and 1120 may be connected through a cable 1113. As shown in FIG. 2, the cable 1113 is fixed to the first body part 1110 and may be connected to the second body part 1120.

Referring to FIG. 2, the first body part 1110 includes a thigh band body 1111, a main control unit 1112, a connector and a cable 1113, a belt fixing part 1114a, 1114b, a first electrical stimulation part 1115, a stimulation ceramic connector 1116, and a muscle movement measurement ceramic 1117.

The thigh band body 1111 marks the position of the knee when wearing (A), so users can easily wear it. The main control unit 1112 can control the operation of the first and second body parts 1110, 1120. The main control unit 1112 can be implemented on a printed circuit board (PCB). The main control unit 1112 may include an operating button for operating the wearable device 1100. In addition, the main control unit 1112 may include a display device for displaying the operating state of the wearable device 1100, and a display control device for controlling the display device may be provided. The construction and operation principle of the main control unit 1112 will be explained in more detail in FIG. 4.

The connector and cable 1113 may be connected to the main control unit 1112, and may include a cable for connection with the second body part 1120. The connector and cable 1113 may include a port for charging a battery. The connector and cable 1113 can be implemented in several ways. For example, the connector and cable 1113 may be connected to the second body part 1120 through a USB-C type connection port, or may charge the battery using a USB-C type charging port.

The belt fixing parts 1114a and 1114b may be used when the first body part 1110 is worn and fixed to the thigh. The belt fixing parts 1114a and 1114b may be fixed using a fixing barkle 1114b, as shown in FIG. 2. The belt fixing parts 1114a and 1114b may fix the wearable device 1100 to the thigh in a manner other than the fixing barkle 1114b.

The first electrical stimulation part 1115 may apply electrical stimulation to the thigh. The first electrical stimulation part 1115 may apply an electric current to the thigh to relieve muscle pain or induce a muscle strengthening exercise. The first electrical stimulation part 1115 may collect a user's biological signal (eg, an EMG signal) or transmit a signal for electrical muscle stimulation (EMS) or nerve dominant muscle electrical stimulation (NMES) to the user's muscles.

The first electrical stimulation part 1115 may include an electrical stimulation pad. The electrical stimulation pad can be used for single use in a wet form. Alternatively, the electrical stimulation pad may be manufactured using a dry high-adhesive material to transmit a user's biological signal or an electrical stimulation signal of a nerve dominant muscle. For example, the electrical stimulation pad may be made of a conductive dry adhesive electrode pad using a carbon nano material.

Referring to FIG. 3, the second body part 1120 includes a shank band body 1121, a connector connection part 1122, a belt fixing part 1123a, 1123b, a second electrical stimulation part 1125, a magnetic pole connection part 1126, and a muscle movement measuring device 1127.

The shank band body 1121 indicates the position of the knee when worn (B), so that the user can easily wear it. The connector connection part 1122 may be connected to the cable 1113 of the first body part 1110. The belt fixing parts 1123a and 1123b may be used when fixing the second body part 1120 to the shank. The second electrical stimulation part 1125 may apply electrical stimulation to the shank. The second electrical stimulation part 1125 may apply an electrical stimulation signal of the nerve dominant muscle to the shank. The second electrical stimulation part 1125 may include an electrical stimulation pad. In FIGS. 2 and 3, the stimulation ceramic connection parts 1116, 1126 and the muscle movement measurement ceramics 1117, 1127 are ceramics for measuring the movement of the thigh or shank.

Figure 4:
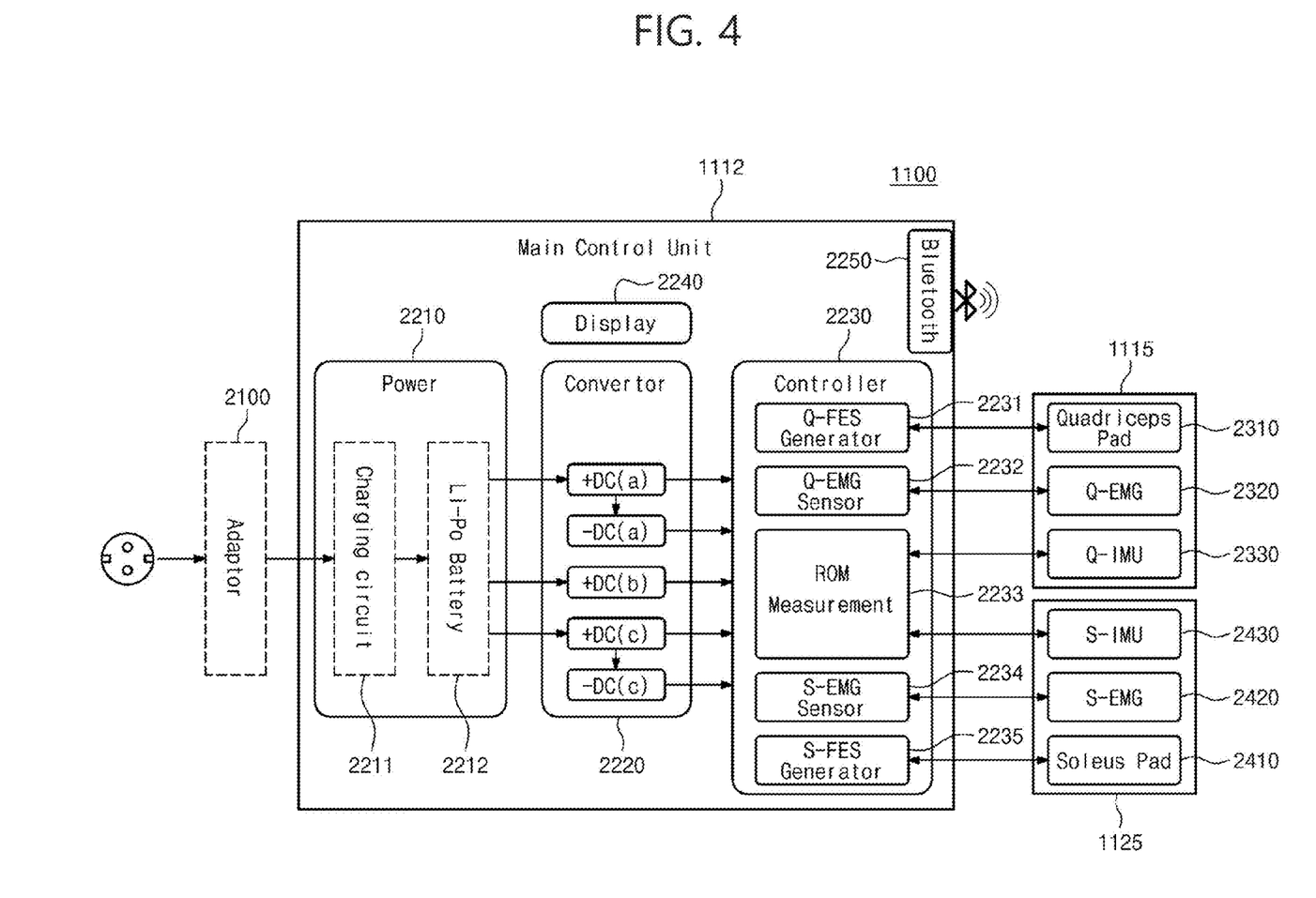
FIG. 4 is a block diagram illustrating an exemplary configuration of the wearable device illustrated in FIGS. 2 and 3.

FIG. 4 is a block diagram illustrating an exemplary configuration of the wearable device illustrated in FIGS. 2 and 3. Referring to FIG. 4, the wearable device 1100 includes a main control unit 1112, a first electrical stimulation part 1115, and a second electrical stimulation part 1125.

The main control unit 1112 may include a power supply 2210, a converter 2220, a controller 2230, a display unit 2240, and a communication unit 2250. The main control unit 1112 may be supplied with power through the adapter 2100. The adapter 2100 may receive AC power (eg, 220V AC power) and output DC power (eg, 5V DC power).

The power supply 2210 may include a charging circuit 2211 and a battery 2212. The charging circuit 2211 may receive 5V DC power from the adapter 2100 and charge the battery 2212. The charging circuit 2211 may have an overcharge protection function. The battery 2212 may be a lithium-polymer battery. The battery 2212 is used as an operating power source of the wearable device 1100 and may provide DC power (eg, 3.7V DC power) of a certain level. The battery 2212 may have a predetermined charge amount (eg, 800 mAh).

The converter 2220 may be converted to voltages of several levels, such as +DC (a) V, −DC (a) V, +DC (b) V, +DC (c) V, −DC (c) V of the battery 2212. For example, the converter 2220 may convert the DC voltage (DC) of +5V, −5V, +3V, +18V, −18V. The converted DC voltage may be used as a driving power source of the controller 2230.

The controller 2230 may include stimulation signal generation circuits 2231 and 2235, leg motion measurement and sensing circuits 2232 and 2234, and joint angle measurement circuit 2233. The stimulation signal generation circuits 2231 and 2235 may generate an electrical stimulation signal of a nerve dominant muscle for functional electrical stimulation (FES). The stimulation signal generation circuits 2231 and 2235 may include a Q-FES generator 2231 for applying functional electrical stimulation to the thigh muscles and an S-FES generator 2235 for applying functional electrical stimulation to the shank muscles.

The leg motion measurement sensing circuits 2232 and 2234 may be an EMG (eledromyogram) measurement sensing circuit. The leg motion measurement sensing circuits 2232 and 2234 may include a Q-EMG sensor 2232 for thigh EMG measurement sensing and an S-EMG sensor 2234 for shank EMG measurement sensing. The joint angle measurement circuit 2233 may measure a range of motion (ROM) of the knee.

The display unit 2240 may display a charging state of the battery 2212 or an operating state of the controller 2230. The display unit 2240 may be implemented as an LED. Meanwhile, the display unit 2240 may be included in the controller 2230.

The communication unit 2250 may communicate with a user electronic device (refer to FIG. 1, 1200). The communication unit 2250 may provide measurement information (ie, rehabilitation exercise information) by the controller 2230 to the user electronic device 1200. Also, the communication unit 2250 may receive feedback on the provided measurement information from the user electronic device 1200.

In FIG. 4, the communication unit 2250 is shown to communicate through Bluetooth. However, the communication unit 2250 includes Code Division Multiple Access (CDMA), Global System for Mobile Communication (GSM), Wideband CDMA (WCDMA), CDMA-2000, Time Division Multiple Access (TDMA), Long Term Evolution (LTE), and Wimax (Worldwide Interoperability for Microwave Access), WLAN (Wireless LAN), UWB (Ultra Wide Band), WI-DI (Wireless Display), WiFi, etc. can be used.

Each of the first and second electrical stimulation parts 1115 and 1125 may transmit functional electrical stimulation (FES) to the user's muscles. Here, the functional electrical stimulation may be neuromuscular electrical stimulation (NMES). The first electrical stimulation part 1115 may apply an electrical stimulation signal of the nerve dominant muscle generated by the Q-FES generator 2231 to the thigh muscle using the thigh electrical stimulation pad 2310. The second electrical stimulation part 1125 may apply the electrical stimulation signal of the nerve dominant muscle generated by the S-FES generator 2235 to the shank muscle using the shank electrical stimulation pad 2410.

The electrical stimulation signal of the nerve dominant muscle may be a low-frequency signal that limits the amount of energy for safety. However, the electrical stimulation signal of the nerve dominant muscle is not limited to a low frequency, and may be a medium or high frequency signal. The electrical stimulation signal of the nerve dominant muscle can stimulate the user's muscles to prevent pain or muscle atrophy. In addition, the intensity, frequency, current or waveform of the electrical stimulation signal of the nerve dominant muscle may be adjusted by the controller 2230 according to the degree of rehabilitation of the user. The controller 2230 may apply stimuli such as current intensity (Amplitude), frequency (Pulse per Seconds), operation width (Pulse Interval), ramp, total time, etc. in a predetermined range.

For example, the current strength is in the range of 0~70 mA (adjustment unit: 1/5/10 mA), the frequency is in the range of 20~999 Hz (control unit: 1/10/100 Hz), and the operating width is 0.1~6.5 s (adjustment unit: 1/5/10 mA). Unit: 1/5/10 s), the lamp is in the range of 1 to 10000 ms (control unit: 1/10/100 ms), and the total operating time is in the range of 1 to 59 m (control unit: 1/5/10 m). The electrical stimulation signal of the nerve dominant muscle can be applied.

In the thigh electrical stimulation pad 2310 and the shank electrical stimulation pad 2410, electrodes for applying electrical stimulation of the nerve dominant muscle and electrodes for detecting a response to the electrical stimulation of the nerve dominant muscle can be arranged in an array form. The controller 2230 may measure an EMG signal through an array-shaped electrode, or may issue a command by selecting a position to transmit an electrical stimulation signal of a nerve dominant muscle.

Each of the first and second electrical stimulation parts 1115, 1125 may include EMG sensors 2320, 2420 and IMU sensors 2330, 2430. The thigh EMG sensor 2320 may measure the thigh EMG, and the shank EMG sensor 2420 may measure the shank EMG. Through the EMG sensors 2320, 2420, it is possible to analyze muscle signal frequency and muscle fatigue.

The IMU sensors 2330, 2430 are sensors for detecting inclination, and can know Euler angles composed of Roll, Pitch, and Yaw, and provide posture data of precise angles. The joint angle measurement circuit 2233 may measure a user's leg movement, that is, a range of motion (ROM), using the thigh IMU sensor 2330 and the shank IMU sensor 2430.

FIG. 5 is a block diagram illustrating a software structure of the user electronic device shown in FIG. 1 by way of example. Referring to FIG. 5, the user electronic device 1200 may be connected through the wearable device 1100 and the communication unit 1210 described in FIG. 4. As an example, the communication unit 1210 may be connected through Bluetooth.

The user electronic device 1200 sets parameters of the wearable device 1100, controls the FES output of the wearable device 1100, or measures and utilizes a range of motion (ROM) or an electromyography (EMG) of the knee. For example, the user electronic device 1200 measures and utilizes a program 1201 for setting FES parameters, a program 1202 for measuring and utilizing electromyography (EMG), and a program 1243 for measuring and utilizing a range of motion (ROM) of the knee.

Also, the user electronic device 1200 may drive a rehabilitation exercise program. The rehabilitation exercise program may include a game program 1204 for playing a game using an electromyogram (EMG) measurement value and a range of motion (ROM) measurement value, and an avatar training program 1205. The avatar training program 1205 may check the progress of the rehabilitation exercise using ROM and EMG measurements. In addition, the avatar training program 1205 may reinforce the intensity of the rehabilitation exercise when the degree of performance of the rehabilitation program is weak through the FES output. The display unit 1230 may display FES parameters setting values, EMG measurements, and ROM measurements. Also, a game or an avatar program may be displayed on the display unit 1230.

Figure 6:
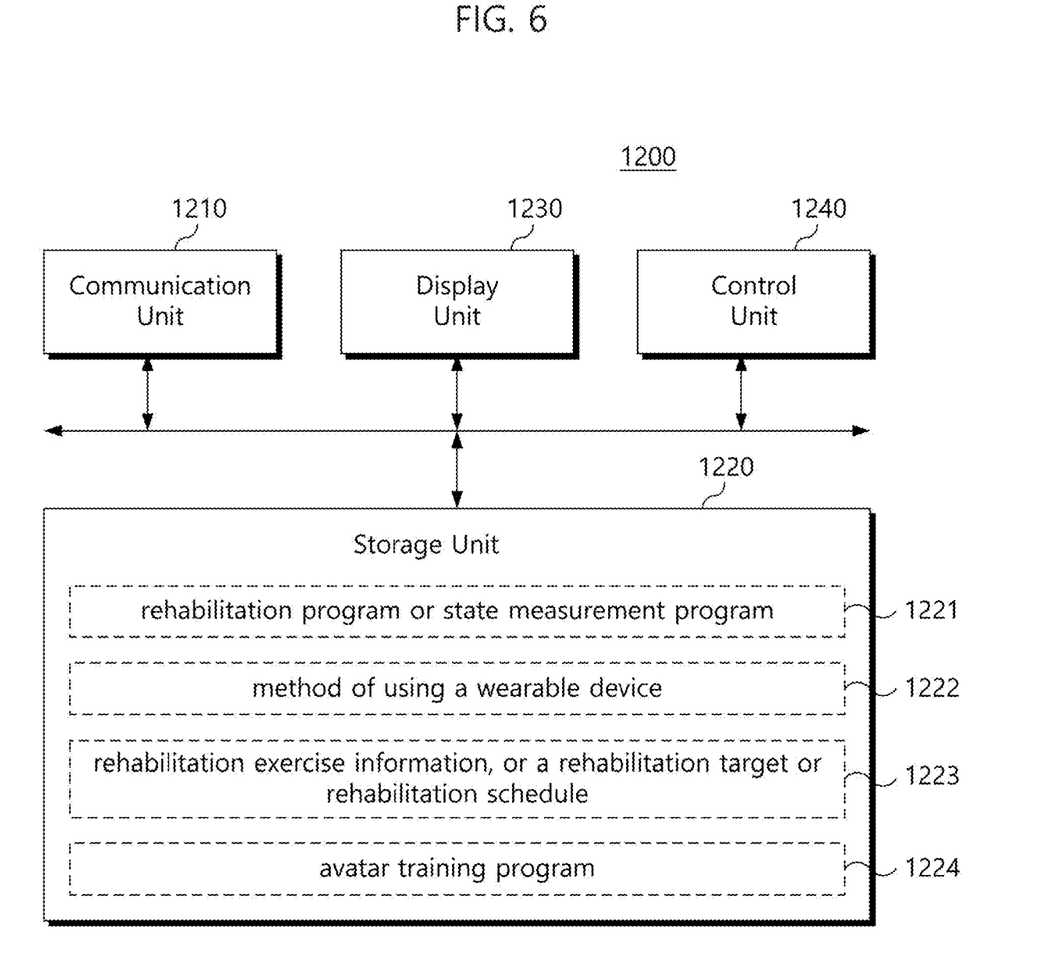
FIG. 6 is a block diagram illustrating an exemplary hardware configuration of the user electronic device shown in FIG. 5.

FIG. 6 is a block diagram illustrating a hardware configuration of the user electronic device shown in FIG. 5 by way of example. Referring to FIG. 6, the user electronic device 1200 may include a communication unit 1210, a storage unit 1220, a display unit 1230, and a control unit 1240.

The communication unit 1210 may receive rehabilitation exercise information from the communication unit 2250 of the wearable device 1100 and a suitable rehabilitation program from a program recommendation server (see FIG. 1, 1300). The communication unit 1210 may transmit the received rehabilitation exercise information to the rehabilitation program recommendation server 1300.

The storage unit 1220 may store information related to rehabilitation, such as a rehabilitation program or state measurement program 1221, a method of using a wearable device 1222, rehabilitation exercise information or a rehabilitation target or rehabilitation schedule 1223. The storage unit 1220 may store at least one rehabilitation program, a state measurement program, and a method of using the wearable device 1100, received from the rehabilitation program recommendation server 1300. Wherein, the state measurement program may be a program for determining the state of the user who starts the rehabilitation exercise for the first time. However, the state measurement program may be used by a user who has previously performed rehabilitation exercises to determine his or her condition.

The storage unit 1220 may store a method of using the wearable device 1100. Further, the storage unit 1220 may store rehabilitation exercise information transmitted from the wearable device 1100. The storage unit 1220 may provide stored information or programs to the display unit 1230 or the control unit 1240 under the control of the control unit 1240.

The storage unit 1220 may store personal information of a user. Here, the personal information may include information for identifying an individual such as a social security number, date of birth, gender, name, password, fingerprint, and health-related information such as height, weight, blood pressure, chronic disease, and age. According to the repetitive rehabilitation exercise, the user may perform a gamified rehabilitation program (refer to FIG. 5, 1204) using the user electronic device 1200. In this case, the user electronic device 1200 may determine whether the current user is a user who has performed an existing rehabilitation exercise with reference to previously stored personal information. If a new user performs a rehabilitation exercise, personal information on the new user may be stored in the storage unit 1220.

The storage unit 1220 may store the avatar training program 1224. The avatar training program 1224 may be already installed in the user electronic device 1200 or may be downloaded and installed from the rehabilitation program recommendation server 1300. The avatar training program 1224 may collect training data such as knee motion range, joint motion speed, joint torque, and surface EMG information through the wearable device 1100. In addition, the avatar training program 1224 may include a standardized data evaluation unit, an electric stimulation part for providing a functional electric stimulation to a user, and a machine learning algorithm.

For example, when the user wears the wearable device 1100, a virtual trainer and a user avatar may be displayed on the display unit 1230 of the user electronic device 1200. Here, the user avatar may reflect the user's movement or movement on the display unit 1230 in real time. The virtual trainer may provide a user with a training guide obtained by using training data such as joint motion range, joint motion speed, joint torque, and surface EMG.

The virtual trainer can show the user a 3D virtual image superimposed on reality (AR: Augmented Reality), a virtual image that is not real (VR: Virtual Reality), or a combination of the two (MR: Mixed Reality). The user may perform rehabilitation exercises while viewing the virtual trainer and the user avatar through the display unit 1230.

The avatar training program 1224 may compare or collate the training data with standardized data directly or indirectly presented by a medical professional or a medical institution. Through this, the avatar training program 1224 derives or sets the current strength (Amplitude), frequency (Pulse per Seconds), operation width (Pulse Interval), ramp, and total time optimized for the user. Electrical stimulation may be given to the user through the wearable device 1100.

The display unit 1230 may display a rehabilitation program, a condition measurement program, a method of using a wearable device, and input of personal information of a user. The display unit 1230 may display the user's rehabilitation exercise result, rehabilitation target, rehabilitation schedule, etc. Through this, the user can check how much the rehabilitation exercise has been performed, the current range of motion (ROM) of the joint in which he can rotate, and the degree of his or her rehabilitation achievement.

The controller 1240 may drive a rehabilitation program or a condition measurement program in the user electronic device 1200 and control these programs to be displayed on the display unit 1230. In addition, the controller 1240 may control the communication unit 1210 to transmit feedback information on rehabilitation exercise information to the wearable device 1100.

Figure 7:
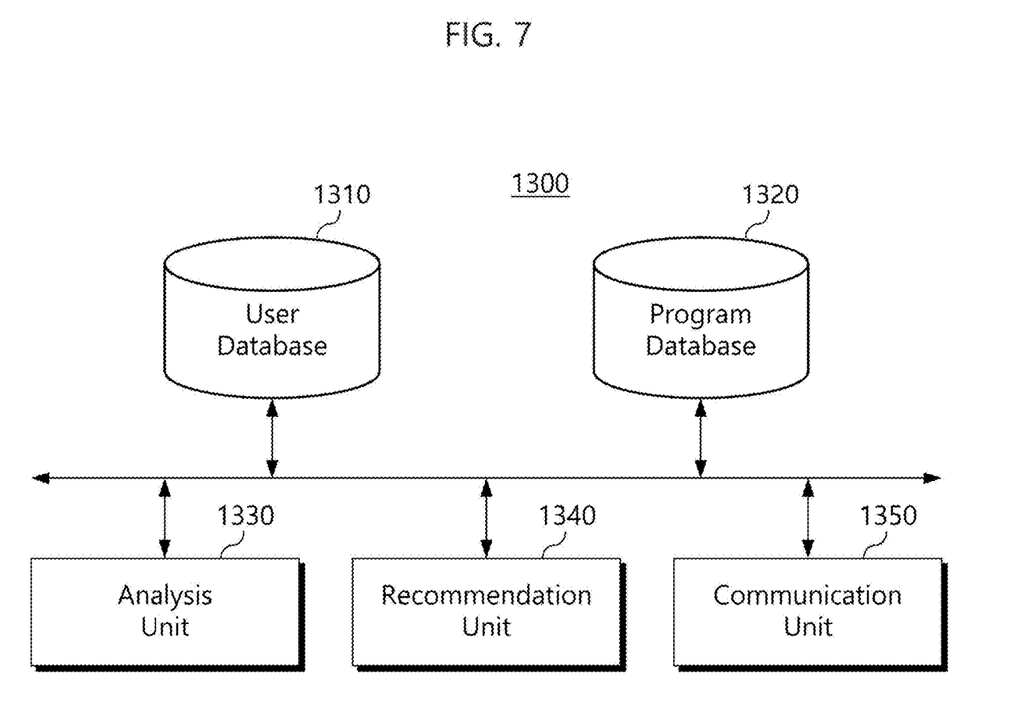
FIG. 7 is a block diagram illustrating an exemplary rehabilitation program recommendation server shown in FIG. 1.

FIG. 7 is a block diagram illustrating an exemplary rehabilitation program recommendation server shown in FIG. 1. Referring to FIG. 7, the rehabilitation program recommendation server 1300 may include a user database 1310, a program database 1320, an analysis unit 1330, a recommendation unit 1340, and a communication unit 1350.

The user database 1310 may store rehabilitation exercise information measured by the wearable device 1100. In this case, the rehabilitation exercise information may be stored in association with the user's personal information. Rehabilitation exercise information stored in the user database 1310 may be classified by the analysis unit 1330. Rehabilitation exercise information may be classified for each individual by the analysis unit 1330 and stored in the user database 1310. The analysis unit 1330 may classify rehabilitation exercise information for each part where the user wears the wearable device 1100 and store it in the user database 1310.

The program database 1320 may store a plurality of rehabilitation programs, a plurality of condition measurement programs, and information on a method of using the wearable device. Also, the program database 1320 may store an avatar training program.

The plurality of rehabilitation programs may have different degrees of difficulty. That is, since each of the users rehabilitation achievement is different, a plurality of rehabilitation programs with different difficulty depending on the rehabilitation achievement can be stored in the program database 1320. Also, a plurality of rehabilitation programs different for each rehabilitation site may be stored in the program database 1320. In addition, a plurality of different rehabilitation programs according to game contents may be stored in the program database 1320.

The plurality of state measurement programs are programs for measuring a user's state. For example, in order to recommend a rehabilitation program suitable for a user who uses the rehabilitation system of the present invention for the first time, a program for measuring the user's condition is required. In addition, a program that measures the user's condition is needed so that the existing user can check to what extent his or her rehabilitation has progressed. Accordingly, before performing the rehabilitation exercise, the user may use the wearable device 1100 according to the condition measurement program displayed on the user electronic device 1200.

The analysis unit 1330 may model a rehabilitation target and a rehabilitation schedule suitable for a user by referring to state information measured by the wearable device 1100 according to a state measurement program. The analysis unit 1330 may analyze the degree of rehabilitation achievement by referring to the rehabilitation exercise information stored in the user database 1310. The analysis unit 1330 may analyze the predicted rehabilitation achievement according to the user's next rehabilitation exercise by referring to the accumulated rehabilitation exercise information. The analysis unit 1330 may readjust a previously modeled rehabilitation target and rehabilitation schedule with reference to the state information and the rehabilitation exercise information.

The analysis unit 1330 may compare rehabilitation exercise information stored in the user database 1310. For example, the analysis unit 1330 may compare a range of motion (ROM) of a knee joint of users. The comparison result of the analysis unit 1330 may be transmitted to the user electronic device 1200. The transmitted comparison result may be provided to the user through the display unit 1230.

The analysis unit 1330 may classify rehabilitation exercise information of various users stored in the user database 1310 by wearing parts of the wearable device 1100. The analysis unit 1330 may analyze the average rehabilitation progress and average rehabilitation achievement of users by referring to the classified rehabilitation exercise information. The analysis unit 1330 may establish an individual rehabilitation schedule and rehabilitation target by referring to the average rehabilitation progress and average rehabilitation achievement of users.

The recommendation unit 1340 may recommend a rehabilitation program suitable for a user from among a plurality of rehabilitation programs by referring to the state information measured by the wearable device 1100 according to the state measurement program. In addition, the recommendation unit 1340 may recommend a rehabilitation program suitable for a user from among a plurality of rehabilitation programs by referring to the analysis result of the analysis unit 1330. At this time, according to the degree of rehabilitation achievement of the user, the previously recommended rehabilitation program may be changed to another rehabilitation program.

The analysis unit 1330 is a machine learning algorithm (machine learning algorithm) to derive the above-described analysis results (rehabilitation target and rehabilitation schedule modeling or readjustment, comparison result, classification result, average rehabilitation progress analysis, average rehabilitation achievement analysis, etc.) learning algorithm) can be used. Similarly, the recommendation unit 1340 may also use a machine learning algorithm for a recommendation operation (derivation of at least one rehabilitation program suitable for a user). To this end, each of the analysis unit 1330 and the recommendation unit 1340 may include a CPU, an AP, or the like, and may be provided in the form of an SoC or an ASIC.

The communication unit 1350 may communicate with the user electronic device 1200 through a network (refer to FIG.

1, 1400). The communication unit 1350 may support wired or wireless communication of various methods described above. The communication unit 1350 receives the rehabilitation exercise information measured by the wearable device 1100 and transfers the analysis result of the analysis unit 1330, the recommendation result of the recommendation unit 1340, or an avatar training program to the user electronic device 1200.

Figure 8:
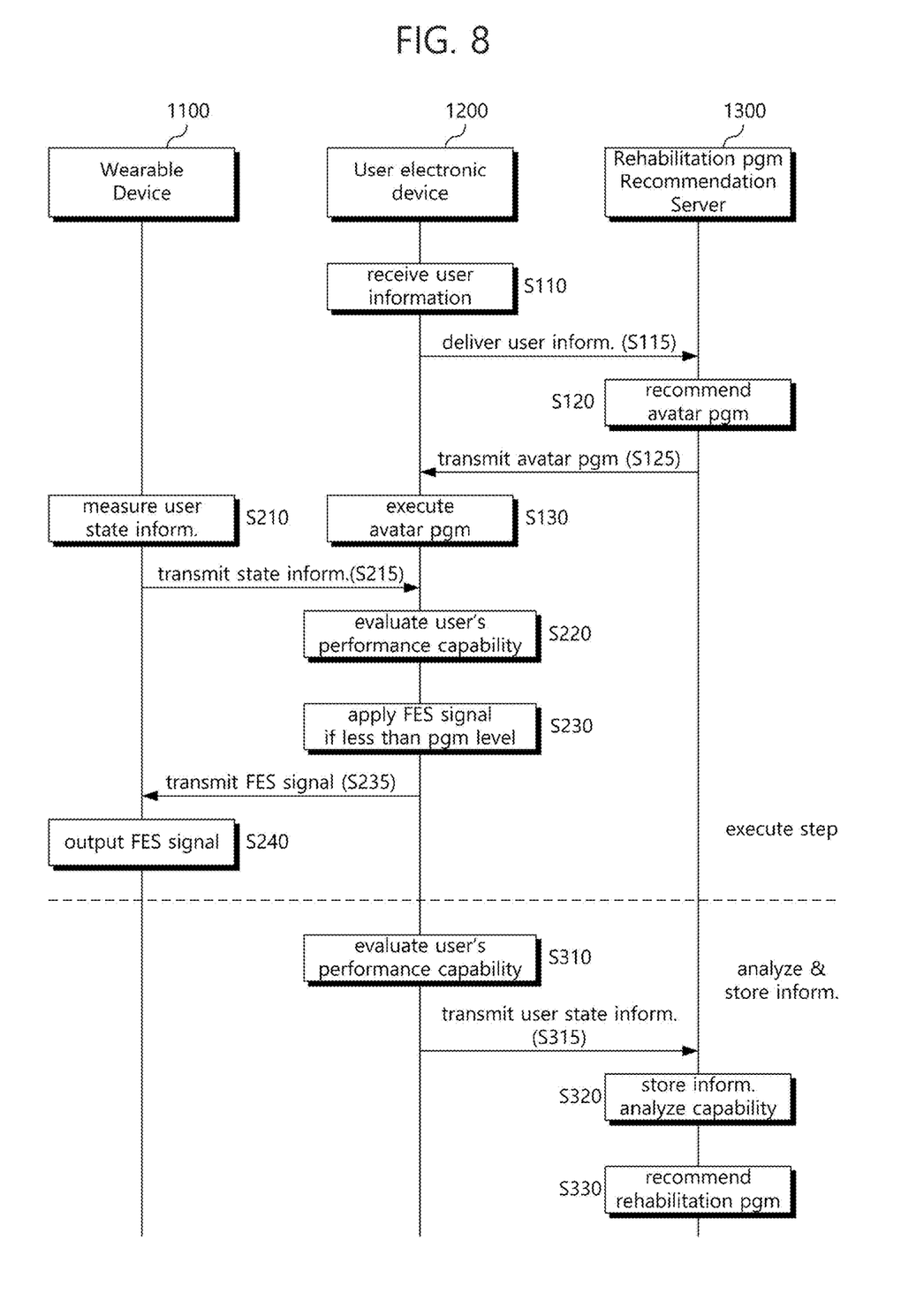
FIG. 8 is a flowchart illustrating a method of operating a rehabilitation system according to an embodiment of the present invention.

FIG. 8 is a flowchart illustrating a method of operating a rehabilitation system according to an embodiment of the present invention. A game character or an avatar may appear on the display unit 1230 of the user electronic device 1200 according to the user's rehabilitation exercise. Hereinafter, an operation in which the avatar training program is performed will be described as an example.

In step S110, the user electronic device 1200 may receive user information. User information may mean the privacy of the aforementioned users. In step S110, the interface for receiving the user's personal information input may be displayed on the display unit 1230.

In step S115, the user electronic device 1200 may be delivered to the rehabilitation program recommendation server 1300 the user information received input. Rehabilitation program recommendation server 1300 may store the received user information. User information may be associated with rehabilitation information in accordance with the rehabilitation of future users.

In step S120, the rehabilitation program recommendation server 1300 may recommend an avatar training program (hereinafter, referred to as the avatar program). Rehabilitation program recommendation server 1300 can derive an avatar program suitable for the user. Recommendation unit 1340 may refer to the previous analysis results of the analysis unit 1330, the most suitable avatar program for the user from a plurality of rehabilitation programs stored in the program database 1320. In step S125, the rehabilitation program recommended server 1300 may transmit the recommended avatar program to the user electronic device 1200.

In step S130, the user electronic device 1200 may execute an avatar program. A virtual trainer and a user avatar may be displayed on the display unit 1230 of the user electronic device 1200. Here, the user avatar may reflect the user's movement or training on the display unit 1230 in real time. The virtual trainer may provide a user with a training guide obtained by using training data such as joint motion range, joint motion speed, joint torque, and surface EMG.

In step S210, the wearable device 1100 may measure user state information performed according to the avatar program. The user's condition information may be rehabilitation information according to rehabilitation. The user's state information can be measured in real time by the wearable device 1100. The wearable device 1100 may measure a range of motion (ROM) or an electromyogram (EMG) of a user's knee joint according to a state measurement program.

In step S215, the wearable device 1100 may transmit user state information to the user electronic device 1200. The wearable device 1100 may transmit user state information to the user electronic device 1200 in real time while the user performs a rehabilitation exercise. The user electronic device 1200 may display user state information on the display unit 1230.

In step S220, the user electronic device 1200 may evaluate the user's program performance capability. The user electronic device 1200 may evaluate to what extent the user performs the avatar program. The user's ability to perform the avatar program may be displayed as a number.

In operation S230, the user electronic device 1200 may control the wearable device 1100 to apply a functional electrical stimulation (FES) signal when the user's ability to perform a program is less than the program level. In step S235, the user electronic device 1200 may transmit an FES signal capable of reaching the program level to the wearable device 1100.

In step S240, the wearable device 1100 may output an FES signal. Referring to FIG. 4, the first electrical stimulation part 1115 may apply an electrical stimulation signal of the nerve dominant muscle generated by the Q-FES generator 2231 to the thigh muscle using the thigh electrical stimulation pad 2310. The second electrical stimulation part 1125 may apply the electrical stimulation signal of the nerve dominant muscle generated by the S-FES generator 2235 to the shank muscle using the shank electrical stimulation pad 2410.

In step S310, the user electronic device 1200 may evaluate the user's performance capability. After applying the FES signal, the user electronic device 1200 may evaluate the user's program performance capability and update the user's state information. The updated state information of the user may be stored in the storage unit 1220 of the user electronic device 1200. Alternatively, the user electronic device 1200 may transmit the updated state information of the user to the rehabilitation program recommendation server 1300 (S315). The wearable device 1100 may directly transmit the measured state information of the user to the rehabilitation program recommendation server 1300.

In step S320, the rehabilitation program recommendation server 1300 may store the received state information and analyze the performance capability. In this case, the received state information may be stored in the user database 1310 in association with the user information received in step S115. The analysis unit 1330 may analyze the current user's state by referring to the user's state information stored in the user database 1310. In particular, in order to analyze the current user's state, the analysis unit 1330 may refer to not only the current user's state information, but also other user's state information or rehabilitation exercise information stored in the user database 1310.

In step S330, the rehabilitation program recommendation server 1300 may recommend a rehabilitation program suitable for the user. The recommendation unit 1340 may recommend one of a plurality of rehabilitation programs stored in the program database 1320 with reference to the analysis result of the analysis unit 1330. The rehabilitation program recommendation server 1300 may transmit the recommended rehabilitation program to the user electronic device 1200.

Figure 9:
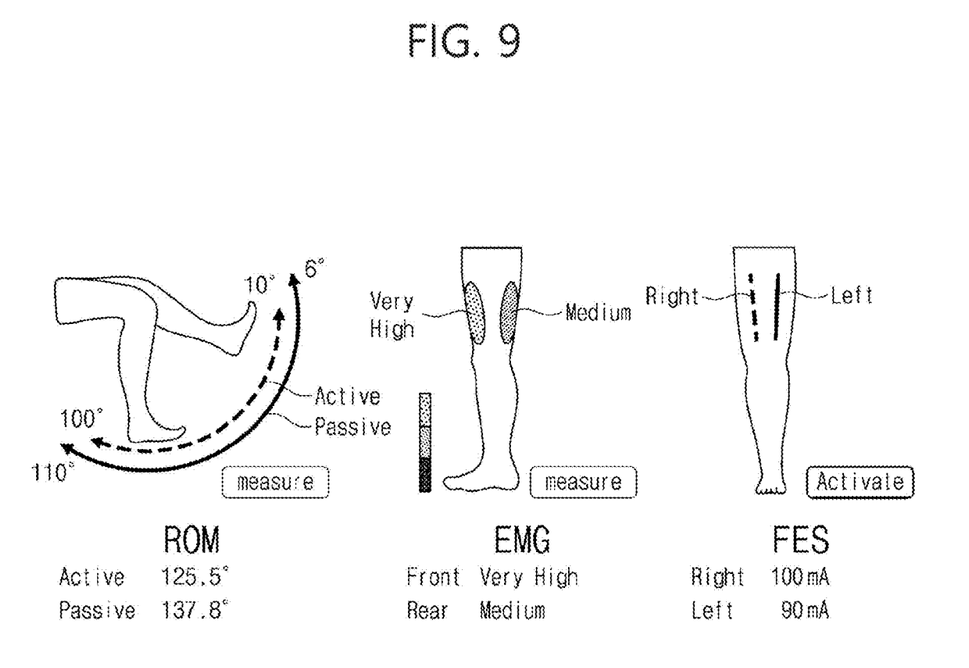
FIGS. 9 and 10 exemplarily show a rehabilitation exercise method of a rehabilitation system according to an embodiment of the present invention.
Figure 10:
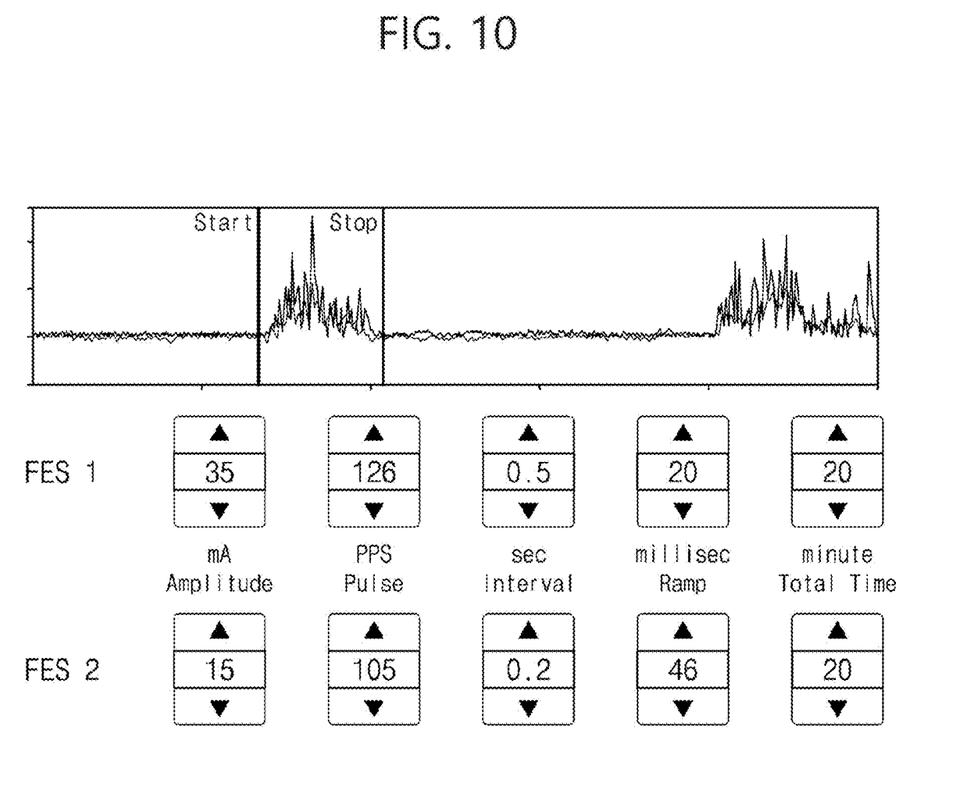

FIGS. 9 and 10 exemplarily show a rehabilitation exercise method of a rehabilitation system according to an embodiment of the present invention. The user may check a current state of a desired rehabilitation body parts, accumulated data, and a degree of improvement of a function through the user electronic device 1200.

Referring to FIG. 9, the user electronic device 1200 may provide information related to a movable range (ROM), an electromyogram (EMG), and functional electrical stimulation (FES) for a user rehabilitation target parts to a user in real time. The range of motion and EMG values are continuously measured during the rehabilitation exercise, and can be automatically updated with the latest information after performing the rehabilitation exercise.

In the case of selectively measuring the range of motion (ROM) and the electromyography (EMG), it is possible to measure again and update the information through 'measure' displayed on the display unit 1230 of the user electronic device 1200. The user electronic device 1200 may include a button unit for performing FES on the display unit 1230. Users can activate FES through the 'Activate' button.

FIG. 10 exemplarily shows a method of using the functional electrical stimulation function shown in FIG. 9. As shown in FIG. 10, the user may apply a functional electrical stimulation while viewing the display unit 1230 of the user electronic device 1200. At this time, the user may increase or decrease the current intensity (Amplitude), frequency (Pulse), operation width (Pulse Interval), ramp, and total time (Total Time), respectively. That is, while the FES is activated, the EMG signal can be checked in real time through the user electronic device 1200. An EMG graph is displayed on the display unit 1230, and a start and a stop of the FES may be displayed on the EMG graph as vertical dividing lines.

The rehabilitation system 1000 according to an embodiment of the present invention may find a stimulation position suitable for a user, set a parameter in which an optimal functional response occurs, and provide a user-customized recommended rehabilitation program through this.

The rehabilitation system 1000 may find an optimized stimulation location for each user by changing the stimulation position until a functional response (eg, joint angle or muscle activity) set as a target is obtained. The rehabilitation system 1000 changes parameters such as current intensity (Amplitude), frequency (Pulse per Seconds), operation width (Pulse Interval), ramp, and total time to optimize functional response (e.g. For example, it is possible to set a parameter in which the joint angle or muscle activity) appears. The rehabilitation system 1000 may perform a user-customized rehabilitation exercise based on an optimized electrode position and parameter.

The rehabilitation system 1000 may perform a joint angle recovery exercise by measuring a range of motion (ROM) of a knee joint. The rehabilitation system 1000 applies electrical stimulation when the range of motion is less than the reference, or provides a user-customized rehabilitation exercise program, thereby effectively performing joint angle recovery exercise.

In addition, the rehabilitation system 1000 may perform an isometric exercise through electromyography (EMG) measurement. The rehabilitation system 1000 may measure muscle activity for a predetermined period of time when power is applied to the leg muscles. The rehabilitation system 1000 may apply electrical stimulation or provide a user-customized rehabilitation exercise program when the muscle activity of the isometric exercise is less than a reference.

The above descriptions are specific examples for carrying out the present invention. In addition to the above-described embodiments, the present invention will include simple design changes or embodiments that can be easily changed. In addition, the present invention will also include techniques that can be easily modified and implemented using the embodiments. Therefore, the scope of the present invention is limited to the above-described embodiments and should not be defined, and should be determined by the claims and equivalents of the present invention as well as the claims to be described later.

What is claimed is:

1. A rehabilitation system comprising:
   a wearable device measuring user's rehabilitation exercise information; and
   a user electronic device receiving an avatar training program recommended based on user personal information and the rehabilitation exercise information from a rehabilitation program recommendation server, receiving the rehabilitation exercise information from the wearable device, and driving the avatar training program,
   wherein the wearable device comprises,
   a first body part worn on a first joint part and having a first electrical stimulation part; and
   a second body part connected to the first body part, worn on a second joint part, and having a second electrical stimulation part,
   wherein the first and second electrical stimulation parts include an electrical stimulation pad in which electrodes for applying electrical stimulation of a nerve dominant muscle and electrodes for sensing a response to the electrical stimulation of the nerve dominant muscle are arranged in an array form,
   wherein the first and second electrical stimulation parts select a position to apply the electrical stimulation signal of the nerve dominant muscle using the electrical stimulation pads arranged in the array form, apply electrical stimulation of a nerve dominant muscle to the first joint muscle or the second joint muscle, and detect its response,
   wherein a main control unit is included in at least one of the first and second body parts,
   wherein the main control unit comprises,
   a stimulation signal generating circuit including a first functional electrical stimulation generator for generating an electrical stimulation signal of the nerve dominant muscle and applying electrical stimulation of the nerve dominant muscle to the first joint muscle of a selected position, and a second functional electrical stimulation generator for applying electrical stimulation of the nerve dominant muscle to the second joint muscle of a selected position;
   a motion measurement sensing circuit including a first EMG sensor for measuring the first joint EMG and a second EMG sensor for measuring the second joint EMG; and
   a joint angle measurement circuit measuring a range of motion (ROM) of a joint angle.

2. The rehabilitation system of claim 1,
   wherein the first and second body parts are connected through a cable,
   wherein the main control unit further comprises,
   a power supply unit having a charging circuit having an overcharge protection function and a battery charged by the charging circuit, and providing operating power to the first and second body parts using the battery;
   a converter configured to convert an operating voltage of the battery into voltages of various levels to generate driving power;
   a display unit for indicating a state of charge of the battery or an operation state of the wearable device; and
   a communication unit for communicating with the user electronic device,
   wherein the main control unit drives the stimulation signal generation circuit, the motion measurement sensing circuit, and the joint angle measurement circuit using the driving power of the converter.

3. The rehabilitation system of claim 2,
   wherein the first joint part is a thigh, the second joint part is a shank, and the first and second body parts have a knee display part.

4. The rehabilitation system of claim 3,
wherein the first and second electrical stimulation parts include EMG sensors for measuring EMG, and analyze muscle signal frequency and muscle fatigue through the EMG sensors.

5. The rehabilitation system of claim 4,
wherein the first and second electrical stimulation parts include IMU sensors for detecting inclination, and measure a range of motion of the joint angle of the knee through the IMU sensors.

6. The rehabilitation system of claim 2,
wherein the wearable device applies an electrical stimulation signal of a nerve dominant muscle by determining a current intensity, a frequency, an operation width, a ramp, and a range of the total operation time.

7. The rehabilitation system of claim 1,
wherein the user electronic device executes the avatar training program, and evaluates a user's program execution capability based on user state information.

8. The rehabilitation system of claim 7,
wherein the user electronic device controls the wearable device to reach the program level by generating an FES signal when the user's program execution capability is less than the program level.

9. A rehabilitation system comprising:
a wearable device measuring rehabilitation exercise information of a user;
a user electronic device receiving the rehabilitation exercise information from the wearable device and driving a gamified rehabilitation program; and
a rehabilitation program recommendation server receiving user personal information and the rehabilitation exercise information from the wearable device or the user electronic device, recommending one or more gamified rehabilitation programs from among a plurality of rehabilitation programs based on the user personal information and the rehabilitation exercise information, and providing the recommended gamified rehabilitation program to the user electronic device,
wherein the wearable device comprises,
a first body part worn on a first joint part and having a first electrical stimulation part; and
a second body part connected to the first body part, worn on a second joint part, and having a second electrical stimulation part,
wherein the first and second electrical stimulation parts include an electrical stimulation pad in which electrodes for applying electrical stimulation of a nerve dominant muscle and electrodes for sensing a response to the electrical stimulation of the nerve dominant muscle are arranged in an array form,
wherein the first and second electrical stimulation parts select a position to apply the electrical stimulation signal of the nerve dominant muscle using the electrical stimulation pads arranged in the array form, apply electrical stimulation of a nerve dominant muscle to the first joint muscle or the second joint muscle, and detect its response,
wherein a main control unit is included in at least one of the first and second body parts,
wherein the main control unit comprises,
a stimulation signal generating circuit including a first functional electrical stimulation generator for generating an electrical stimulation signal of the nerve dominant muscle and applying electrical stimulation of the nerve dominant muscle to the first joint muscle of a selected position, and a second functional electrical stimulation generator for applying electrical stimulation of the nerve dominant muscle to the second joint muscle of a selected position;
a motion measurement sensing circuit including a first EMG sensor for measuring the first joint EMG and a second EMG sensor for measuring the second joint EMG; and
a joint angle measurement circuit measuring a range of motion (ROM) of a joint angle.

10. The rehabilitation system of claim 9,
wherein the first joint part is a thigh, the second joint part is a shank, and the first and second body parts have a knee display part.

* * * * *